United States Patent
Huo

(10) Patent No.: US 7,417,146 B2
(45) Date of Patent: *Aug. 26, 2008

(54) FACIAL TRIS-CYCLOMETALLATED GROUP 9 COMPLEX SYNTHESIS

(75) Inventor: Shouquan Huo, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 564 days.

This patent is subject to a terminal disclaimer.

(21) Appl. No.: 11/015,910

(22) Filed: Dec. 17, 2004

(65) Prior Publication Data

US 2006/0135772 A1    Jun. 22, 2006

(51) Int. Cl.
*C07F 15/00* (2006.01)
(52) U.S. Cl. ............................................. 546/4
(58) Field of Classification Search ............... 546/4
See application file for complete search history.

(56) References Cited

U.S. PATENT DOCUMENTS

2001/0019782 A1    9/2001   Igarashi et al.
2003/0068526 A1    4/2003   Kamatani et al.

OTHER PUBLICATIONS

S. Huo, "Synthesis for Organometallic Cyclometallated Transition Metal Complexes", U.S. Appl. No. 10/729,207, (D-87050) filed Dec. 5, 2003.
A. B. Tamayo, et al., "Synthesis and Characterization of Facial and Meridional Tris-cyclometalated Iridium(III) Complexes", J. Am. Chem. Soc., 2003, pp. 7377-7387.

*Primary Examiner*—Zinna N Davis
(74) *Attorney, Agent, or Firm*—Arthur E. Kluegel

(57) ABSTRACT

A process for forming a facial tris-cyclometallated rhodium or iridium complex isomer from a meridional isomer comprises subjecting the meridional isomer to an isomerization reaction in the presence of an acid, an organic solvent, and silica particles.

30 Claims, No Drawings

FACIAL TRIS-CYCLOMETALLATED GROUP 9 COMPLEX SYNTHESIS

FIELD OF THE INVENTION

This invention relates to a chemical reaction for the preparation of a facial tris-cyclometallated a rhodium or iridium complex wherein the complex in the meridional form is isomerized to form the facial form.

BACKGROUND OF THE INVENTION

Cyclometallated iridium complexes have been the focus of research and development in OLED (organic lighting-emitting diode, Ching W. Tang et al, *Applied Physics Letters*, 1987, 51, 913) display devices over last several years. Those complexes can offer higher efficiency when used as phosphorescent dopants in OLED devices since both singlet and triplet excitons generated by electroexcitation can be harvested by a phosphorescent dopant, while only singlets (25% of total excitons) can be utilized when a fluorescent material is used as a dopant. Tris-cyclometallated iridium complexes have demonstrated such advantage. There exist two stereoisomers in homoleptic tri-cyclometallated iridium complexes such as tris(2-(phenyl)pyridinato, N,C$^2$)iridium (III) (Ir(ppy)$_3$), namely facial and meridional isomers as shown below. The facial isomer has been shown to be more desirable as it has demonstrated higher quantum yield and thermal stability than the corresponding meridional isomer (A. B. Tamayo, et al, *J. Am. Chem. Soc.* 2003, 125, 7377).

There are continuous efforts to develop new phosphorescent dopants for improving the efficiency and operational stability of OLED devices. Mixed tris-cyclometallated iridium complexes have recently attracted attention of research community and their applications to OLED devices have been demonstrated (T. Igarashi et al, US 2001/0019782 A1; J. Kamatani, et al, US 2003/0068526 A1; S. Akiyama et al, JP2003-192691A). However, the synthesis of those mixed ligand complexes is challenging. The method employed in the prior art involves the reaction of a bis-cyclometallated iridium complex with a third ligand in glycerol at high temperature (usually above 180° C.), which was found to produce an undesirable mixture of different homoleptic and heteroleptic tris-cyclometallated iridium complexes formed from ligand-scrambling side reactions which leads to difficulties in separation and purification of the desired compounds. Recently, a method was developed in U.S. Ser. No. 09/729,207 to prepare mixed tris-cyclometallated iridium complexes in high yields and purity, but the products obtained from that reaction are meridional isomers. Also, it was discovered that some meridional isomers could be isomerized to their facial isomers by applying heat, but the high temperature required (above 180° C.) was accompanied by severe decomposition in some cases.

It is a problem to be solved to provide an improved process for efficiently isomerizing meridional mixed tris-cyclometallated rhodium or iridium complexes to their facial isomers by reducing the extent of side reactions and high temperature degradation.

SUMMARY OF THE INVENTION

The invention provides a process for forming a facial tris-cyclometallated rhodium or iridium complex isomer from a meridional isomer that comprises subjecting the meridional isomer to an isomerization reaction in the presence of an acid, an organic solvent, and silica particles. The process is particularly suitable for some mixed tris-cyclometallated rhodium or iridium complexes since formation of ligand-scrambling by products is minimized under the isomerization conditions. The process is mild and operationally simple and enables the isolation of desired pure facial compounds.

DETAILED DESCRIPTION OF THE INVENTION

The invention is summarized above.

Tris-cyclometallated complexes related to the invention may be represented by one of the following formulas:

$$ML_3 \qquad (1)$$

$$M(L')_2L'' \qquad (2)$$

$$ML'L''L''' \qquad (3)$$

wherein M is the metal Ir or Rh, L, L', L", and L''' are monoanionic bidentate ligands that can be coordinated to M through a carbon and a heteroatom donor. The invention particularly relates to a process for forming a facial tris-cyclometallated iridium or rhodium complex isomer of formula M(piq)$_2$(ppy) from the meridional isomer comprising subjecting the meridional isomer to an isomerization reaction

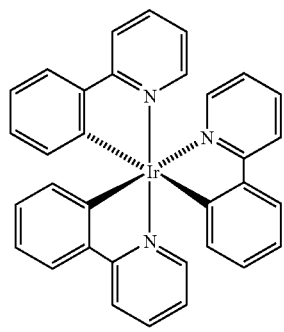

meridional Ir(ppy)$_3$

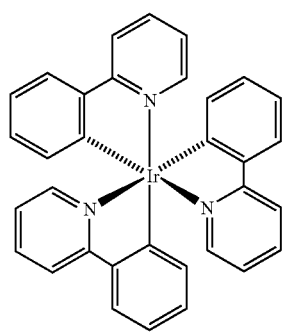

facial Ir(ppy)$_3$ in the presence of an acid, and silica particles, wherein M is iridium or rhodium, piq is a 1- or 3-phenylisoquinoline group, and ppy is a 2-phenylpyridine group as represented by Equation 1:

than two. Examples of mer- and fac-isomers of mixed tris-cyclometallated iridium complex $(1\text{-piq})_2\text{Ir(ppy)}$ are shown below:

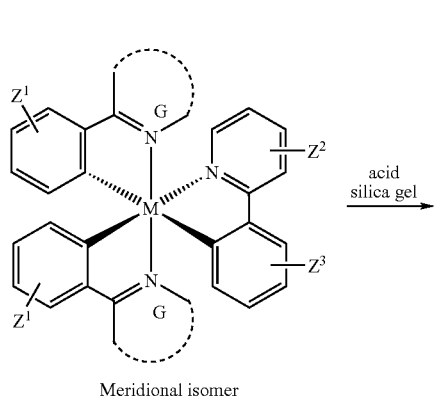

Meridional isomer
(1)

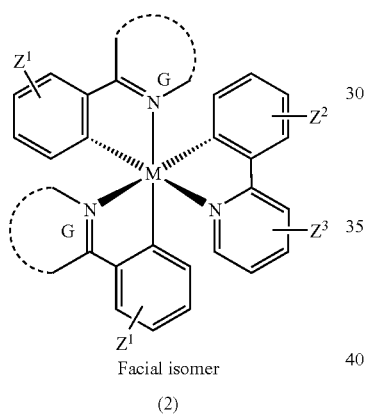

Facial isomer
(2)

wherein,

M represents Ir or Rh, preferably Ir,

G represents an isoquinoline group, and $Z^1$, $Z^2$, and $Z^3$ represent hydrogen or one or more independently selected groups.

The facial isomer is defined as the stereoisomer of a tris-cyclometallated iridium complex wherein three monoanionic bidentate ligands coordinate to the metal with a facial arrangement of the three heteroatom donors and a facial arrangement of the three carbon donors. Similarly, the meridional isomer has a meridional arrangement of the three heteroatom donors and a meridional arrangement of the three carbon donors. As mentioned before, there exist two stereoisomers in homoleptic tris-cyclometallated iridium complexes where three ligands are the same, namely a facial and a meridional isomer. However, when three ligands that coordinate to the iridium are different from each other or two are the same and the third one is different, a mixed tris-cyclometallated iridium complex is formed and the total number of meridional and facial isomers of this compound may be more

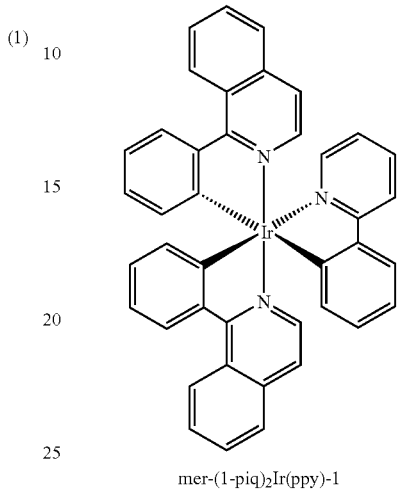

mer-$(1\text{-piq})_2\text{Ir(ppy)}$-1

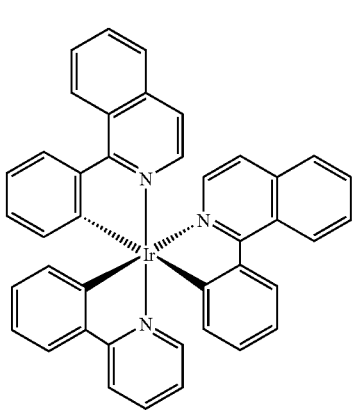

mer-$(1\text{-piq})_2\text{Ir(ppy)}$-2

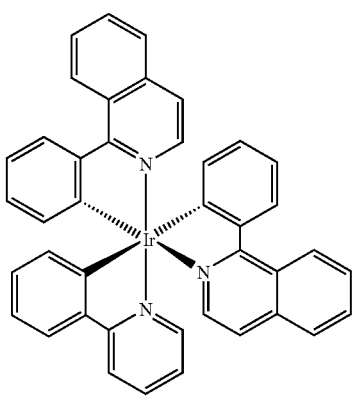

mer-$(1\text{-piq})_2\text{Ir(ppy)}$-3

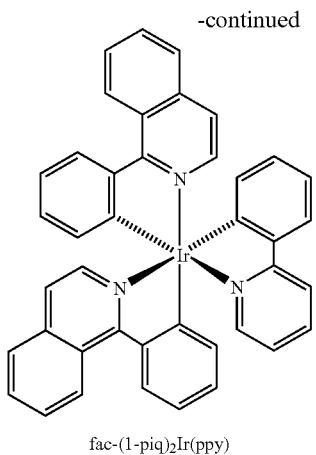

fac-(1-piq)₂Ir(ppy)

The piq ligand can be a 1-phenylisoquinoline or a 3-phenylisoquinoline group as represented by the following formulas,

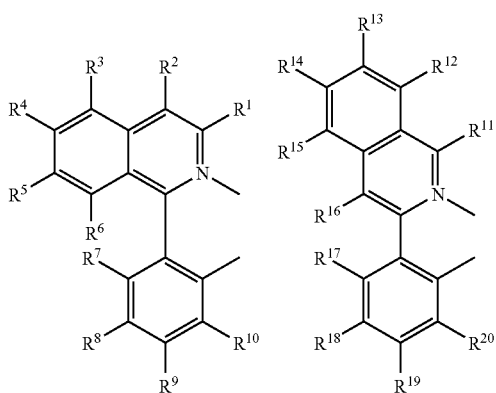

wherein $R^1$-$R^{20}$ represent hydrogen or independently selected substituents. Suitably, the piq ligand is 1-phenylisoquinoline or 3-phenylisoquinoline.

The ppy can be a 2-phenylpyridine group as represented by the following formula,

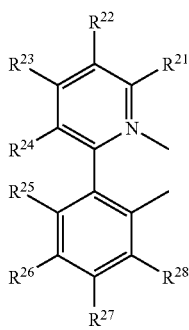

wherein $R^{21}$-$R^{28}$ represent hydrogen or independently selected substituents, provided $R^{21}$ and $R^{22}$, $R^{22}$ and $R^{23}$, $R^{23}$ and $R^{24}$, $R^{24}$ and $R^{25}$, $R^{25}$ and $R^{26}$, $R^{26}$ and $R^{27}$, as well as $R^{27}$ and $R^{28}$ can form a ring group. Conveniently, the ppy group can be chosen from the substituted or unsubstituted forms of the following:

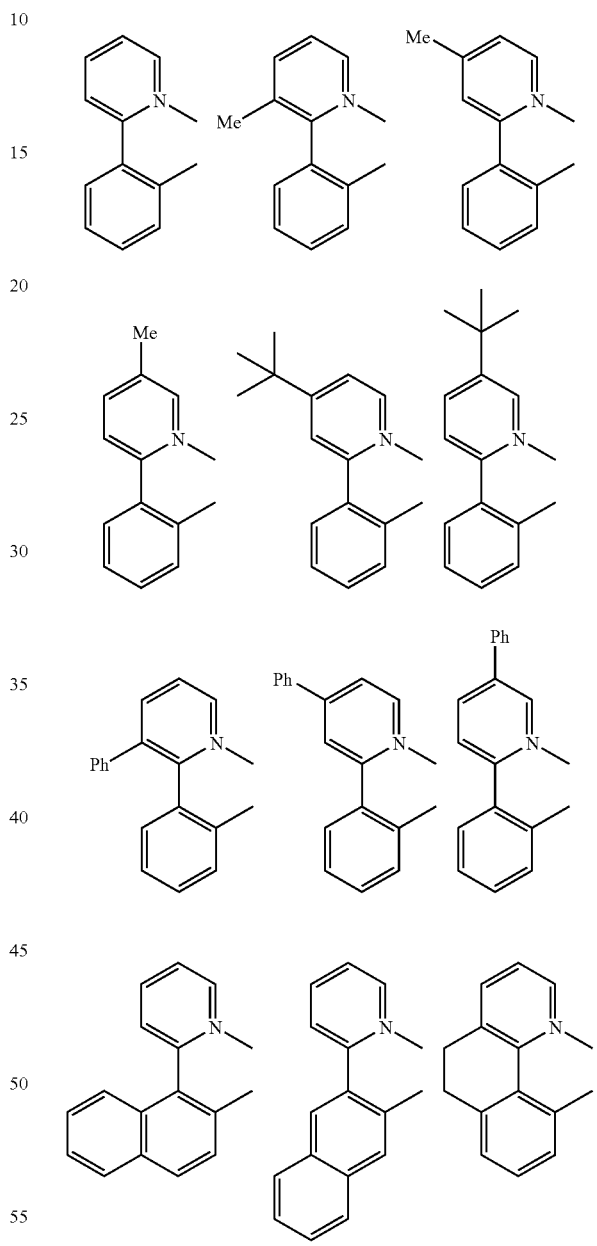

The precursors for the isomerization process, namely meridional tris-cyclometallated iridium complexes Ir(piq)₂(ppy), can be prepared according to the procedure described in the prior art by reacting an organozinc complex of a desired organic ligand with a suitable halide-bridged di-nuclear bis-cyclometallated iridium complex (U.S. Ser. No. 10/729,207). They may also be prepared by other published methods (A. B. Tamayo, et al, *J. Am. Chem. Soc.* 2003, 125, 7377). Some representative meridional complexes are shown below, -continued
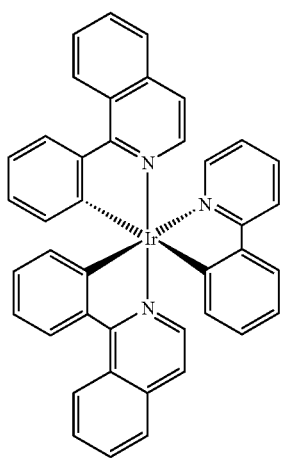
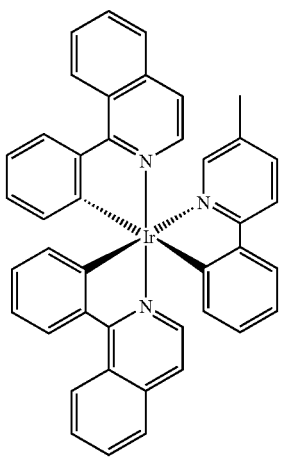
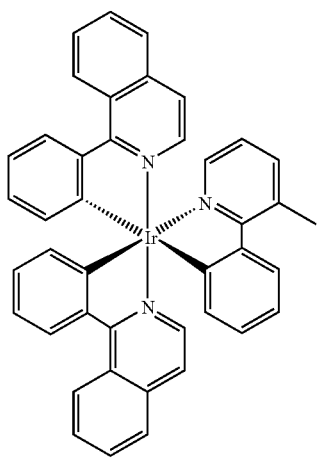
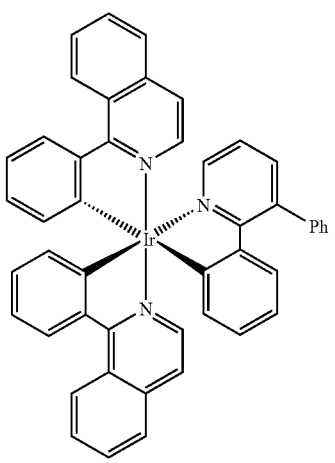
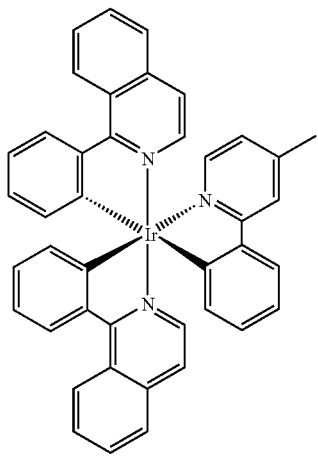
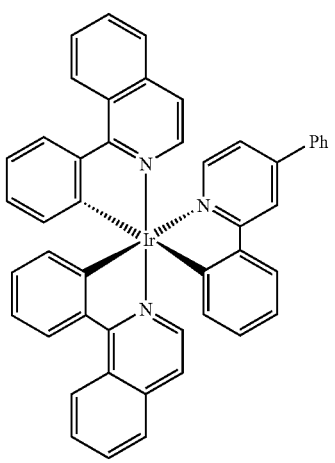

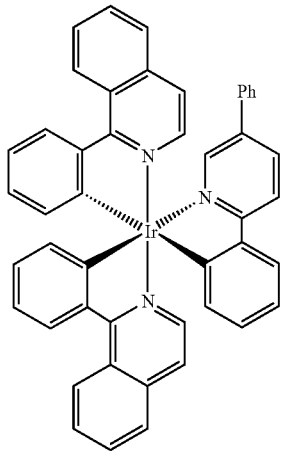
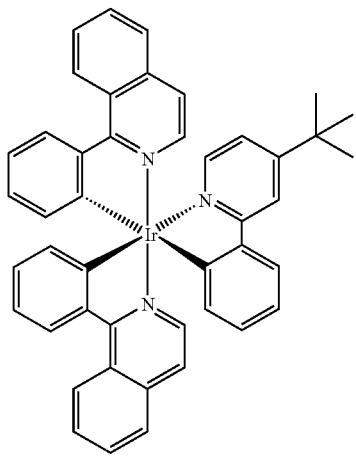
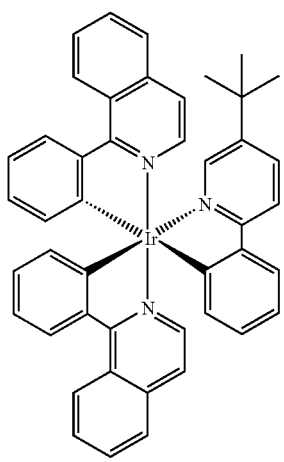
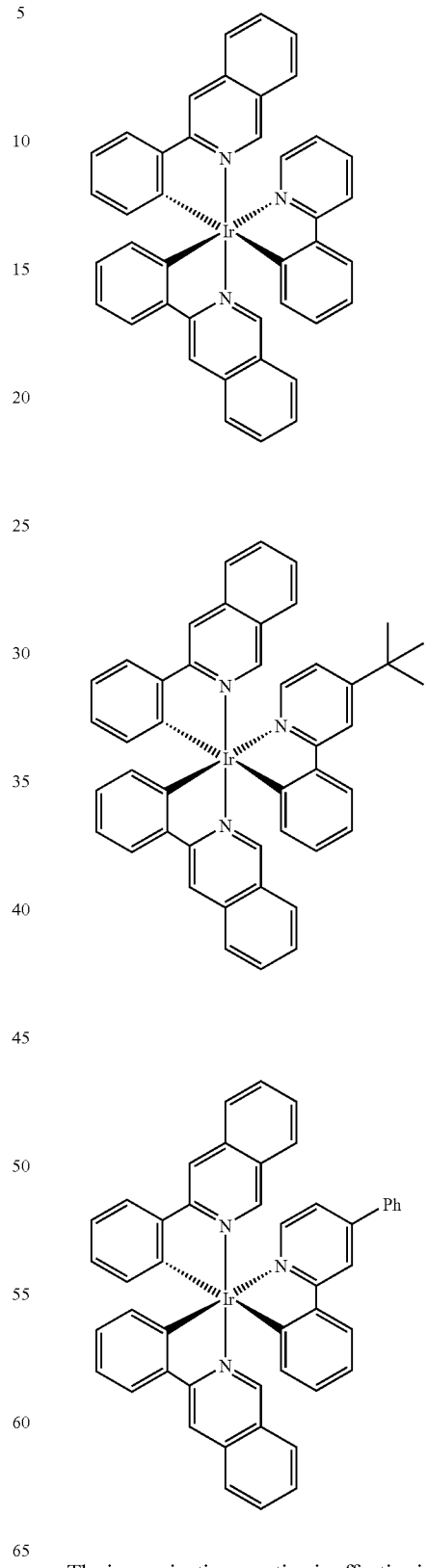
The isomerization reaction is effective in the presence of an acid. The acid can be an organic or inorganic acid. Suitably, the acid can be an aliphatic acid or an aromatic acid and can be represented by the formula RCOOH wherein R is a 1-8 carbon alkyl group or an aryl group. For example, R can be an alkyl group that can be further substituted and R can be a phenyl group that can be further substituted. Desired examples of acid represented by RCOOH are acetic acid, propionic acid, butyric acid, benzoic acid, oxalic acid, malonic acid, and malic acid. Conveniently, the acid is acetic acid.

Suitable examples of inorganic acids are hydrochloric acid, hydrobromic acid, carbonic acid, sulfuric acid, sulfurous acid, phosphoric acid, and phosphorous acid. Conveniently, the acid is hydrochloric acid. Other acids may also be used in the reaction. The acid can be used in a catalytic or an excess amount in the reaction, namely in 0.1 to 10 equivalents or higher relative to the starting iridium compound. An organic acid can be used as a co-solvent.

Addition of silica particles promotes the reaction. Suitable silica particles are silica gel particles. Conveniently, the silica gel of the size between 60-400 mesh can be used. The amount of silica gel used in the reaction can vary in a broad range for obtaining optimal results. The particles serve to promote the reaction and the amount is selected so as to enable the desired reaction rate.

The reaction can be performed in an organic solvent. Suitable organic solvents include halogenated alkanes or arenes. Conveniently, the solvent is methylene chloride or 1,2-dichloroethane. The isomerization can be performed between 0° C. and 100° C. Conveniently, the reaction can be performed at ambient temperature and is complete within about 24 hours or longer depending on the amount of the acid and the silica gel used in the reaction. The reaction can also be performed at 0° C. or below.

Decompositions are also observed to produce more polar materials that can be easily separated from the desired product. Significantly, the formation of ligand-scrambling by-products in the isomerization of mixed tris-cyclometallated iridium complexes is negligible. Therefore, a high purity of the desired facial isomer can be attained readily, which is critical to the performance of OLED devices. Isomeric purity is defined as relative amount of the facial isomer to the total amount of both facial and meridional isomers. A high isomeric purity of >98% of facial compounds can be obtained from the reaction. Further, the purity of the desired compound can be improved to >99% through sublimation, recrystallization or other means.

Unless-otherwise specifically stated, use of the term "group", "substituted" or "substituent" means any group or radical other than hydrogen. Additionally, when reference is made in this application to a compound or group that contains a substitutable hydrogen, it is also intended to encompass not only the unsubstituted form, but also its form further substituted with any substituent group or groups as herein mentioned, so long as the substituent does not destroy properties necessary for the intended utility. Suitably, a substituent group may be halogen or may be bonded to the remainder of the molecule by an atom of carbon, silicon, oxygen, nitrogen, phosphorous, or sulfur. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy)propyl, cyclohexyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecyl-benzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, hydrophobic groups, solubilizing groups, blocking groups, and releasing or releasable groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

SYNTHETIC EXAMPLES the reaction mixture in one portion. Anhydrous dichloromethane (30 mL) was added. After the mixture was refluxed for 6 hours, any remaining organozinc reagent was quenched with 5 mL of methanol. The mixture was poured into water (200 mL) and extracted with dichloromethane (3×100 mL). The combined organic layers were washed with water (2×100 mL) and brine (200 mL) and dried over $MgSO_4$. After filtration, the solvents were evaporated and the crude materials were dissolved in minimum amount of hot dichloromethane. Addition of methanol led to the precipitation of the product, which was collected by filtration, washed thoroughly with methanol and diethyl ether, and dried in air to yield yellow orange solids, meridional bis-(1-phenylisoquinoline-$C^2$,N) (phenylpyridinato-$C^2$,N) iridium (III), 1.85 g, 82%. The meridional configuration of the titled compound has been confirmed by X-ray crystal structure analysis.

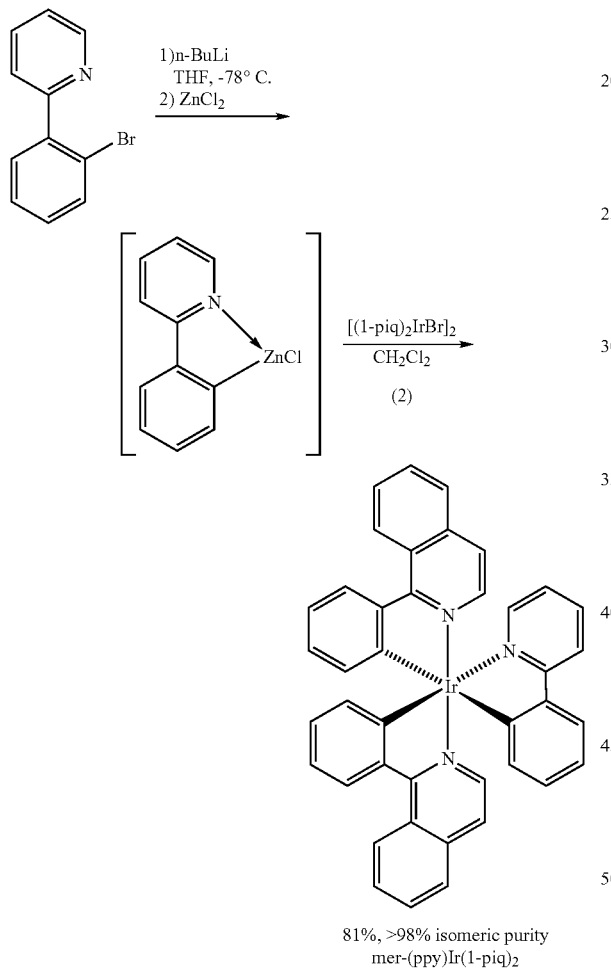

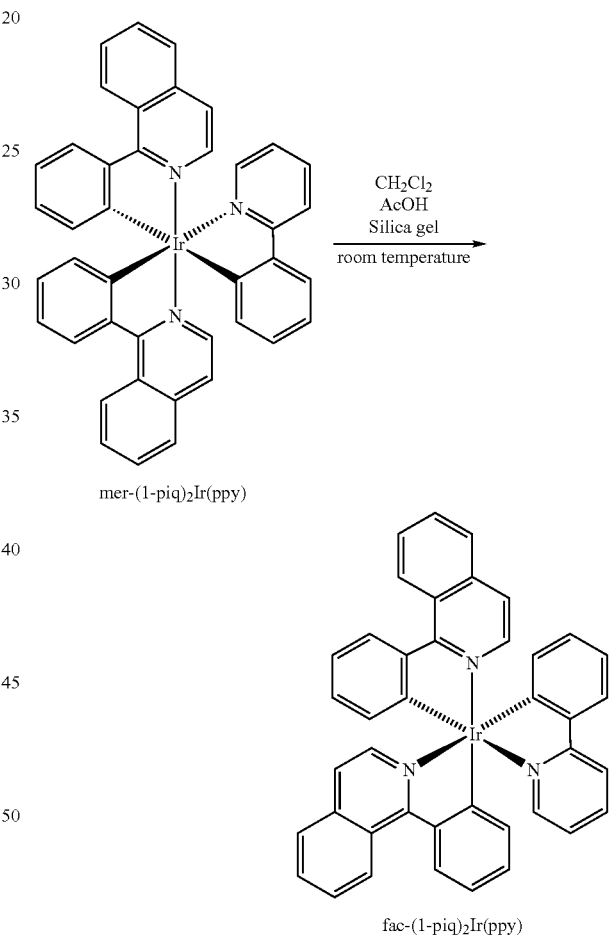

Synthesis of meridional tris-cyclometallated iridium complex, mer-(1-piq)$_2$Ir(ppy): A solution of 1-(2-bromophenyl) pyridine (1.8 g, 7.5 mmol) in anhydrous THF (30 mL, Aldrich) was cooled to −78° C. with a dry ice-acetone bath. To this solution was added dropwise a solution of n-BuLi in hexanes (5.2 mL, 1.6 M, 8.3 mmol, Aldrich). The mixture was stirred at −78° C for 30 min and a solution of ZnCl$_2$ in ether (7.5 mL, 1.0 M, 7.5 mmol, Aldrich) was added slowly via a syringe. The cooling bath was removed and the reaction mixture was warmed to about room temperature. The bromide-bridged dimer [Ir(piq)$_2$Br]$_2$ (2.03 g, 1.5 mmol) was added to Isomerization of meridional tris-cyclometallated iridium complex, mer-(piq)$_2$Ir(ppy): A mixture of mer-(piq)$_2$Ir(ppy) (300 mg, 0.4 mmol), dichloromethane (30 mL), acetic acid (48 mg, 0.8 mmol), and silica gel (2 g, 60-200 mesh, Aldrich) was stirred at room temperature for 24 h. The mixture was filtered through a short column packed with silica gel and washed with dichloromethane. The filtrate was concentrated and addition of methanol led to the precipitation of the product. The precipitates were collected by filtration, washed with methanol and ether, and dried in air to yield 110 mg of facial bis-(1-phenylisoquinoline-C$^2$,N)(phenylpyridinato-C$^2$,N) iridium (III) ((piq)$_2$Ir(ppy)), 37%, >98% HPLC isomeric purity. The material was sublimed at 270° C. to give deep red crystals with >99% HPLC isomeric purity. A single crystal was selected for X-ray structure analysis, which confirmed the facial arrangement of the three nitrogen donors in the complex.

It should be mentioned that the reaction conditions described in the examples are not optimized and one skilled in the field can make some improvements by extensively optimizing the reaction parameters for each individual reaction.

The patents and other publications referred to in this description are incorporated herein by reference in their entirety.

The invention claimed is:

1. A process for forming a facial tris-cyclometallated rhodium or iridium complex isomer from a meridional isomer comprising subjecting the meridional isomer to an isomerization reaction in the presence of an acid, an organic solvent, and silica particles.

2. The process of claim 1 wherein the tris-cyclometallated complex is represented by one of the following formulas:

  (1)

  (2)

  (3)

wherein M is the metal Ir or Rh, L, L', L", and L'" are monoanionic bidentate ligands that can be coordinated to M through a carbon and a heteroatom donor.

3. The process of claim 2 wherein at least one ligand includes an aromatic ring and a heterocyclic ring.

4. The process of claim 3 wherein the heterocyclic ring includes a nitrogen atom for coordinating to the metal complex.

5. The process of claim 4 wherein the ligand includes one derived from the substituted or unsubstituted forms of the following:

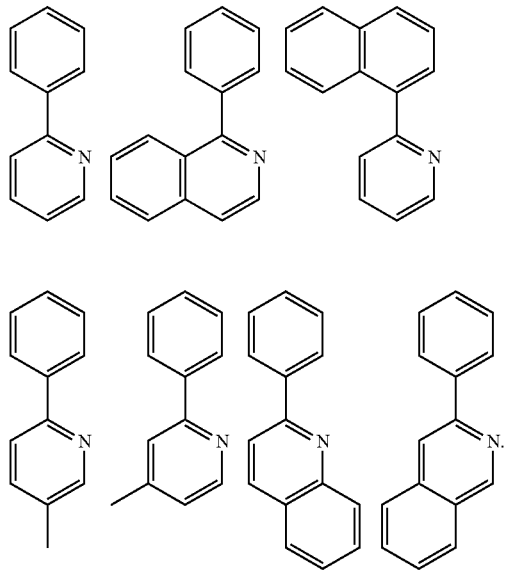

6. The process of claim 1 wherein the meridional tris-cyclometallated complex is an iridium complex that contains tree identical ligands.

7. The process of claim 1 wherein the meridional tris-cyclometallated complex is an iridium complex that contains two or three different ligands.

8. The process of claim 7 wherein at least one of the ligands is a 1-phenylisoquinoline or a 3-phenylisoquinoline group.

9. The process of claim 8 wherein at least one of the ligands is a 1-phenylisoquinoline represented by the formula:

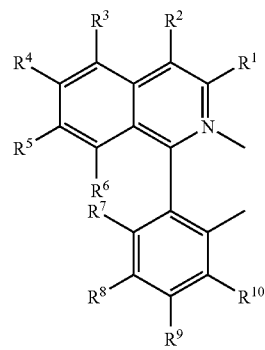

wherein R$^1$-R$^{10}$ represent hydrogen or independently selected substituents.

10. The process of claim 8 wherein at least one of the ligands is a 3-phenylisoquinoline represented by the formula:

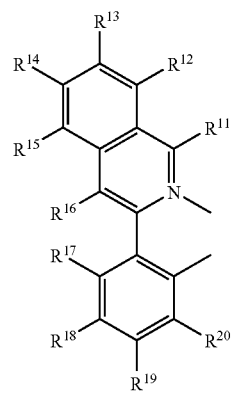

wherein R$^{11}$-R$^{20}$ represent hydrogen or independently selected substituents.

11. The process of claim 9 wherein two of the ligands are 1-phenylisoquinoline ligands and the other is a phenylpyridine group.

12. The process of claim 11 wherein the phenylpyridine ligand group is one selected from the substituted or unsubstituted forms of the following groups:

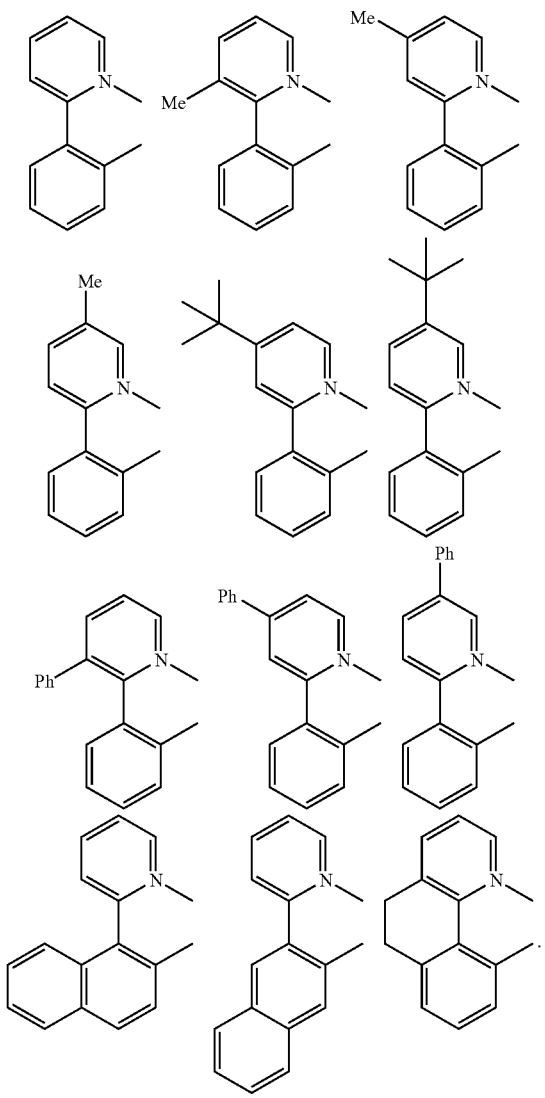

13. The process of claim 1 wherein the organic solvent comprises a halogenated hydrocarbon.

14. The process of claim 13 wherein the solvent comprises an alkyl halide.

15. The process of claim 13 wherein the solvent comprises methylene chloride or 1,2-dichloroethane.

16. The process of claim 1 wherein the acid is an organic acid.

17. The process of claim 16 wherein the organic acid is represented by the formula RCOOH wherein R is a 1-8 carbon alkyl group or an aryl group.

18. The process of claim 16 wherein the organic acid comprises acetic acid, propionic acid, butyric acid, benzoic acid, oxalic acid, malonic acid, or malic acid.

19. The process of claim 18 wherein the acid comprises acetic acid.

20. The process of claim 1 wherein the acid is an inorganic acid.

21. The process of claim 20 wherein the inorganic acid is hydrochloric acid.

22. The process of claim 1 wherein the acid is a Brönsted acid.

23. The process of claim 1 wherein the acid is a Lewis acid.

24. The process of claim 1 wherein the silica particle is silica gel.

25. The process of claim 24 wherein the size of the silica gel particle is larger than 60 mesh.

26. The process of claim 24 wherein the size of silica gel is smaller than 400 mesh.

27. The process of claim 24 wherein the size of the silica gel particles is between 60 and 400 mesh.

28. The process of claim 1 wherein the reaction is carried out for a period of time sufficient to form the facial isomer in >95% isomeric purity.

29. The process of claim 1 wherein the reaction is carried out for a period of time sufficient to form the facial isomer in >98% isomeric purity.

30. The process of claim 1 wherein the reaction product is further purified by sublimation or recrystallization.

* * * * *

UNITED STATES PATENT AND TRADEMARK OFFICE
CERTIFICATE OF CORRECTION

| | | |
|---|---|---|
| PATENT NO. | : 7,417,146 B2 | Page 1 of 1 |
| APPLICATION NO. | : 11/015910 | |
| DATED | : August 26, 2008 | |
| INVENTOR(S) | : Shouquan Huo | |

It is certified that error appears in the above-identified patent and that said Letters Patent is hereby corrected as shown below:

Claim 6, line 3             "tree" should be replaced with --three--.

Signed and Sealed this

Thirtieth Day of December, 2008

JON W. DUDAS
*Director of the United States Patent and Trademark Office*

UNITED STATES PATENT AND TRADEMARK OFFICE
CERTIFICATE OF CORRECTION

PATENT NO. : 7,417,146 B2  
APPLICATION NO. : 11/015910  
DATED : August 26, 2008  
INVENTOR(S) : Shouquan Huo Page 1 of 1

It is certified that error appears in the above-identified patent and that said Letters Patent is hereby corrected as shown below:

Column 16, Claim 6, line 3      "tree" should be replaced with --three--.

This certificate supersedes the Certificate of Correction issued December 30, 2008.

Signed and Sealed this

Third Day of February, 2009

JOHN DOLL  
*Acting Director of the United States Patent and Trademark Office*